(12) United States Patent
Yamashita et al.

(10) Patent No.: US 10,299,757 B2
(45) Date of Patent: May 28, 2019

(54) MEDICAL TUBE, CATHETER, AND METHOD FOR PRODUCING MEDICAL TUBE

(71) Applicant: TERUMO KABUSHIKI KAISHA, Shibuya-ku (JP)

(72) Inventors: Yasunori Yamashita, Shizuoka (JP); Tooru Oota, Shizuoka (JP); Youichi Ito, Shizuoka (JP); Naoko Katou, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 14/080,404

(22) Filed: Nov. 14, 2013

(65) Prior Publication Data
US 2014/0073928 A1    Mar. 13, 2014

Related U.S. Application Data

(63) Continuation of application No. PCT/JP2012/061990, filed on May 10, 2012.

(30) Foreign Application Priority Data

May 17, 2011    (JP) ................................ 2011-110643

(51) Int. Cl.
*A61B 8/00*    (2006.01)
*A61B 8/12*    (2006.01)
(Continued)

(52) U.S. Cl.
CPC ................ *A61B 8/445* (2013.01); *A61B 8/12* (2013.01); *A61M 25/001* (2013.01);
(Continued)

(58) Field of Classification Search
CPC ......... A61B 8/12; A61B 8/445; A61B 8/4461; A61B 5/6852; A61B 17/2202
(Continued)

(56) References Cited

U.S. PATENT DOCUMENTS 6,045,547 A  *  4/2000  Ren ..................... A61M 25/005
                                                    604/264
6,663,614 B1 * 12/2003  Carter ............... A61M 25/0045
                                                    604/264

(Continued)

FOREIGN PATENT DOCUMENTS

EP    0 958 911 A2    11/1999
EP    1 955 724 A1    8/2008
(Continued)

OTHER PUBLICATIONS

International Search Report (PCT/ISA/210) dated Jun. 12, 2012, by the Japanese Patent Office as the International Searching Authority for International Application No. PCT/JP2012/061990.
(Continued)

*Primary Examiner* — Alexandra L Newton
(74) *Attorney, Agent, or Firm* — Buchanan Ingersoll & Rooney PC (57) ABSTRACT

A first tube is a medical tube provided with a first portion, a second portion and a third portion in this order from the proximal end side toward the distal end side and is made of a resin. At the second portion, the outer diameter is smaller than the outer diameter of the first portion and the inner diameter is substantially equal to the inner diameter of the first portion. At the third portion, the outer diameter and the inner diameter are respectively smaller than the outer diameter and the inner diameter of the second portion. In this manner, a medical tube in which the outer diameter of the proximal end side is relatively large and the outer diameter of the distal end side is relatively small while securing the (Continued)

inner diameter having a sufficient size at the distal end side can be provided.

17 Claims, 5 Drawing Sheets

(51) Int. Cl.
*A61M 25/00* (2006.01)
*A61M 25/09* (2006.01)
*B29D 23/00* (2006.01)
*A61M 25/01* (2006.01)

(52) U.S. Cl.
CPC .... *A61M 25/0009* (2013.01); *A61M 25/0023* (2013.01); *A61M 25/0043* (2013.01); *A61M 25/0045* (2013.01); *A61M 25/0054* (2013.01); *A61M 25/09* (2013.01); *B29D 23/00* (2013.01); *A61M 2025/0183* (2013.01)

(58) Field of Classification Search
USPC ............... 600/139, 140, 437, 459, 462, 467
See application file for complete search history.

(56) References Cited

U.S. PATENT DOCUMENTS

2003/0195419 A1 10/2003 Harada
2008/0188832 A1* 8/2008 Tanioka ................. A61B 8/445
   604/525

FOREIGN PATENT DOCUMENTS

| | | |
|---|---|---|
| JP | 2001-299925 A | 10/2001 |
| JP | 2007-000358 A | 1/2007 |
| JP | 3954888 B2 | 8/2007 |
| JP | 2008-229160 A | 10/2008 |
| WO | 2008-006111 A2 | 1/2008 |

OTHER PUBLICATIONS

Supplementary European Search Report and European Search Opinion issued by the European Patent Office dated Mar. 23, 2015 in counterpart European Application No. 12 786 221.7 (7 pgs).

* cited by examiner

MEDICAL TUBE, CATHETER, AND METHOD FOR PRODUCING MEDICAL TUBE

CROSS REFERENCES TO RELATED APPLICATIONS

This application is a continuation of International Application No. PCT/JP2012/061990 filed on May 10, 2012, and claims priority to Japanese Application No. 2011-110643 filed on May 17, 2011, the entire content of both of which is incorporated herein by reference.

TECHNICAL FIELD

The present invention generally relates to a medical tube, a catheter and a method of manufacturing a medical tube.

BACKGROUND DISCUSSION

There is known a catheter which is used for diagnosing the inside of a body lumen by ultrasonic waves by inserting the catheter into the body lumen such as a blood vessel. An example of such a catheter is disclosed in Japanese Patent No. 3954888.

The catheter described in Japanese Patent No. 3954888 includes a catheter main body having a lumen, and a shaft which is inserted into the lumen of the catheter main body and has a ultrasonic oscillation unit which emits ultrasonic waves at the distal end portion. The catheter allows the shaft which is inserted into the lumen of the catheter main body, to rotate around the axis thereof, as well as move in the proximal end direction, and so it is possible to obtain an ultrasonic image of a blood vessel wall. In addition, when the ultrasonic image is obtained, the operation thereof is performed by filling the lumen, that is, in a gap which is formed between the inner circumferential surface of the catheter main body and the outer circumferential surface of the shaft with a liquid, for example, such as physiological salt solution. This gap is to some extent secured larger, to the extent that when filling with a liquid, the filling can be easily and quickly performed.

In a case where the catheter main body is configured by a resin, as a member of the proximal end side of the catheter main body, a tube in which the outer diameter is relatively large in order to secure sufficient rigidity is used. On the other hand, as a member of the distal end side of the catheter main body, a tube in which the outer diameter is relatively small is used, to facilitate inserting into the body lumen, or the like. Then, these tubes are jointed to form the catheter main body. Therefore, the outer diameter of the distal end portion of the tube of the proximal end side needs to be smaller in accordance with the size of the tube of the distal end side.

In addition, the inner diameter of each tube needs to be set to the predetermined value or more so that the resistance does not become big when filling a liquid into the gap between the inner circumferential surface of the catheter main body and the outer circumferential surface of the shaft.

In addition, with the above-described proximal end side tube having the relatively large outer diameter at the proximal end side and being configured such that the outer diameter of the distal end portion is relatively small, the reachability to the deep blood vessel and the flexibility are enhanced, and there is a need to improve priming performance by setting the inner diameter to the predetermined value or more.

Examples of methods of manufacturing a medical tube like the above-described proximal end side tube include grinding, thermoforming, and the like with respect to a tube for processing having a certain outer diameter and a certain inner diameter.

However, in a method involving grinding the outer circumferential surface of the tube for processing, since the outer diameter of the tube for processing does not become the inner diameter or less and the thickness becomes too thin, there is a risk of breaking the tube when using.

In addition, in a method of decreasing the outer diameter and the inner diameter at the same time, by performing thermoforming, with respect the tube for processing, it is difficult to make the outer diameter small while securing the inner diameter to the predetermined value or more.

SUMMARY

Disclosed here is a medical tube in which the outer diameter of the proximal end side is relatively large and the outer diameter of the distal end side is relatively small while ensuring the inner diameter of sufficient size at the distal end side. Also disclosed is a catheter and a method of manufacturing a medical tube.

According to one aspect, a medical tube comprises a tube possessing a proximal end and a distal end, with the tube possessing a first portion, a second portion and a third portion arranged in this order in a direction from a proximal end side toward a distal end side, and with the tube being made of resin. The first portion, the second portion and the third portion each possess an inner diameter and an outer diameter, the outer diameter of the second portion is smaller than the outer diameter of the first portion, and the inner diameter of the second portion is substantially equal to the inner diameter of the first portion. The inner diameter of the third portion is smaller than the inner diameter of the second portion, and the outer diameter of the third portion is smaller than the outer diameter of the second portion.

The medical tube preferably also includes a first taper portion in which the outer diameter is gradually decreased from the proximal end side toward the distal end side between the first portion and the second portion.

The medical tube preferably also has a second taper portion in which the outer diameter and the inner diameter are, respectively, gradually decreased from the proximal end side toward the distal end side between the second portion and the third portion.

The outer circumference of the second portion and the third portion are preferably a portion in which an other tube is coated.

The thickness of the second portion and the thickness of the third portion are preferably substantially equal.

The medical tube is also preferably configured so that: the thickness of the second portion is 11% to 83% of the thickness of the first portion; the outer diameter of the second portion is 76% to 88% of the outer diameter of the first portion; the outer diameter of the third portion is 79% to 96% of the outer diameter of the second portion; and the inner diameter of the third portion is 78% to 99% of the inner diameter of the second portion.

The medical tube is preferably configured so that the outer diameter of the third portion and the inner diameter of the second portion are substantially equal, and the first portion, the second portion, and the third portion are preferably integrally formed of the same material.

The medical tube is preferably configured of a thermoplastic resin and has flexibility.

According to another aspect, a catheter is configured to be inserted into a body lumen to be used and includes a catheter main body having flexibility, in which the catheter main body has the medical tube disclosed here.

The catheter is preferably configured so that a lumen of the medical tube is used as a sensor lumen into which a driveshaft having an image obtaining unit which fetches or obtains an image of the inside of the body lumen is inserted at the distal end side.

In the catheter, it is preferable that the catheter main body be arranged parallel with respect to the sensor lumen and have a guide wire lumen into which a guide wire is inserted.

A method of manufacturing the medical tube includes, a first process of physically or chemically grinding the outer circumferential surface of the distal end portion of a tube for processing, and a second process for conducting thermoforming, with respect to the portion of the distal end side from a middle of a ground portion of the tube for processing, and more reducing the outer diameter and the inner diameter of the portion of the distal end side from the middle of the ground portion than those of the portion of the proximal end side from the middle of the ground portion, in which in the first process, the portion which is not ground becomes the first portion and the portion which is ground becomes the second portion, and in which in the second process, the third portion is formed by performing the thermoforming.

According to a further aspect, a catheter comprises a catheter main body comprised of a first flexible tube, a second flexible tube and a third flexible tube. The first tube is made of resin, possesses a proximal end and a distal end, and possesses a first axially extending portion, a second axially extending portion and a third axially extending portion arranged in this order in a direction from a proximal end side of the first tube toward a distal end side of the first tube. The first portion of the first tube, the second portion of the first tube and the third portion of the first tube each possesses an inner diameter and an outer diameter. The outer diameter of the second portion is smaller than the outer diameter of the first portion, and the inner diameter of the second portion is substantially equal to the inner diameter of the first portion. The inner diameter of the third portion is smaller than the inner diameter of the second portion, and the outer diameter of the third portion is smaller than the outer diameter of the second portion. The second tube axially overlaps a distal end portion of the first tube and a proximal end portion of the third tube, and the second tube possessing an inner surface fixed to the outer surface of the distal end portion of the first tube, with the inner surface of the second tube fixed to the outer surface of the proximal end portion of the third tube.

DETAILED DESCRIPTION

Set forth below is a detailed description of a medical tube, a catheter and a method of manufacturing a medical tube disclosed here, based on preferred embodiments shown in attached drawings. Use of a medical tube disclosed here is not particularly limited, however, to the embodiment and modifications described below. The detailed description below describes the medical tube disclosed here applied to a constituent member of a catheter, that is, a first tube configured as a part of a catheter main body.

In the description which follows, the left side, the right side, the upper side and the lower side in FIG. 1 to FIG. 5 are referred to as "the distal end", "the proximal end", "the upper" and "the lower", respectively.

Figure 1:
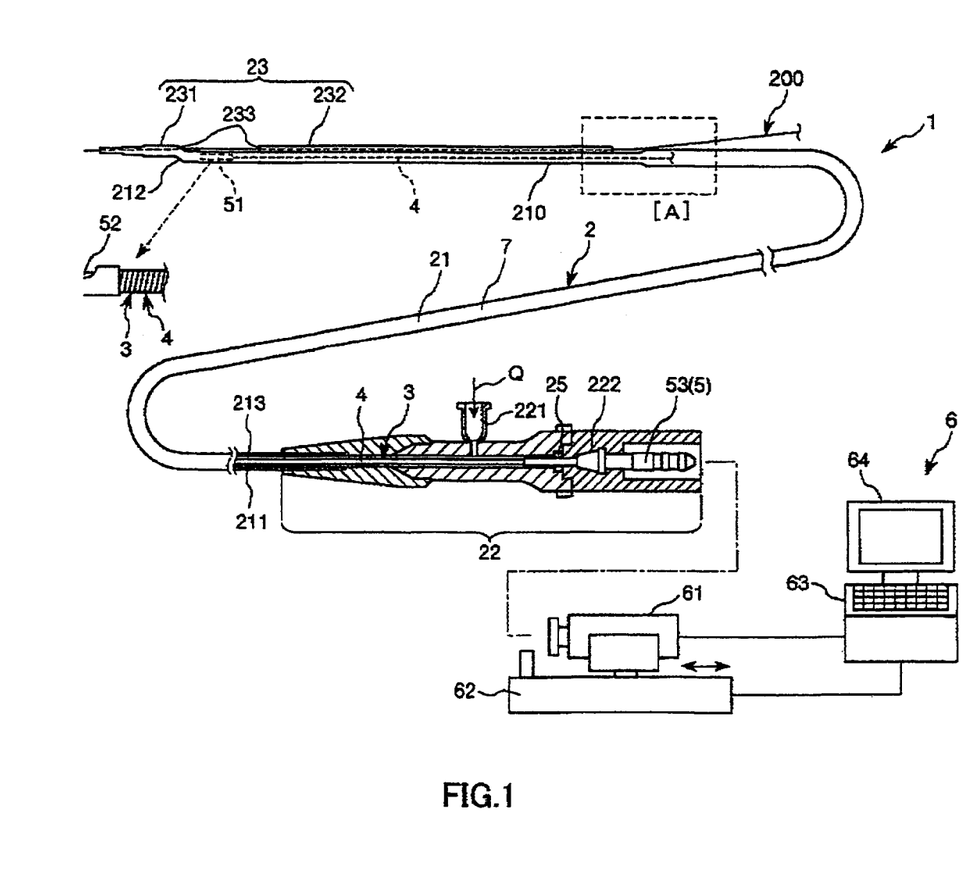
FIG. 1 is a partial longitudinal cross-sectional side view of an embodiment of a catheter assembly including a catheter disclosed here.
Figure 2:
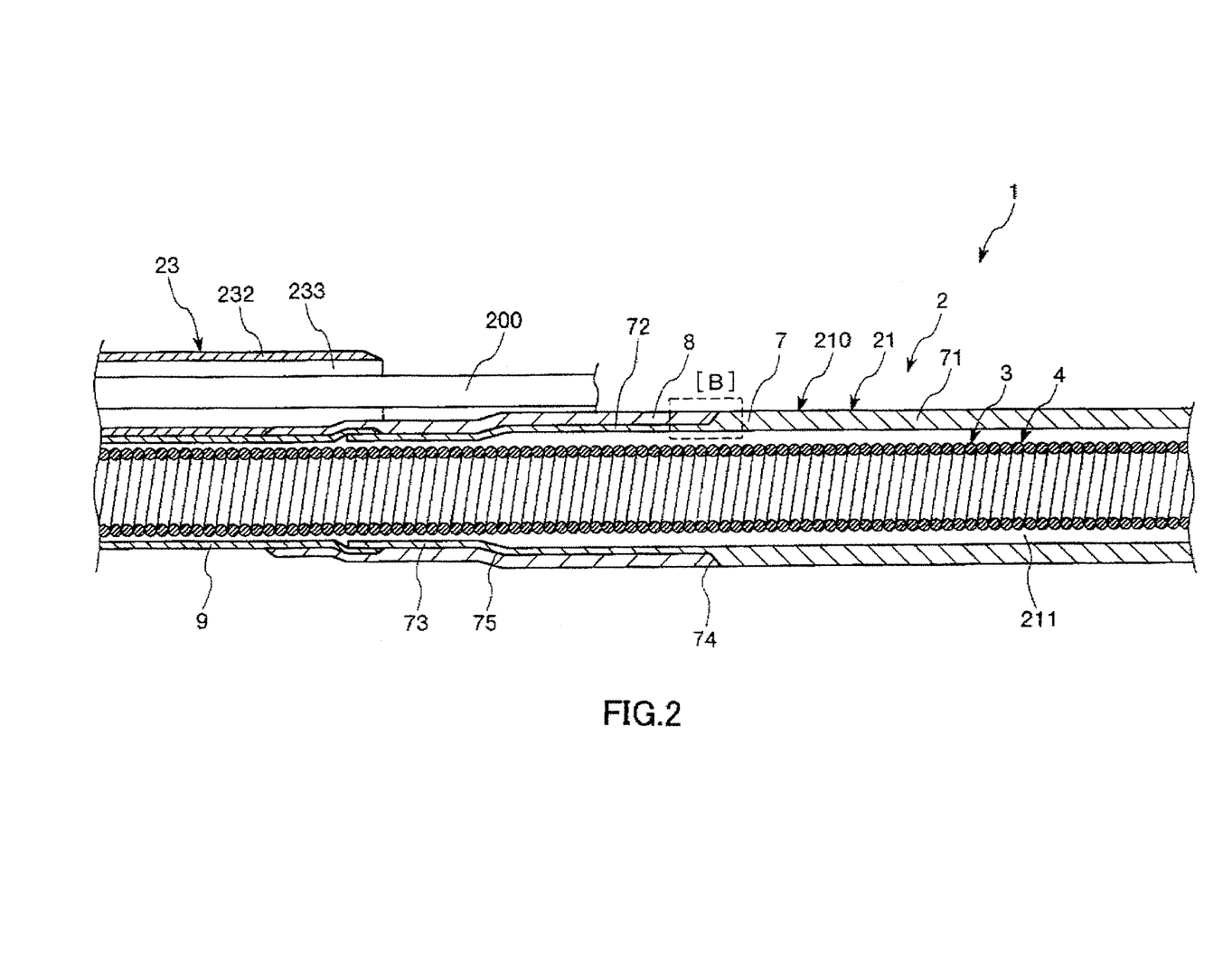
FIG. 2 is an enlarged longitudinal cross-sectional view of an area [A] surrounded with a broken line in FIG. 1.

A catheter assembly 1 shown in FIG. 1 and FIG. 2 includes a catheter 2 and a driveshaft 3, with the drive shaft 3 being inserted into and positioned inside the catheter 2. The catheter assembly 1 is shown in an assembled state in which the catheter 2 and the driveshaft 3 are assembled, and is used by inserting into the body lumen (hereinafter, typically "a blood vessel") to obtain an image of the blood vessel wall which is an internal image of the blood vessel.

In addition, this catheter assembly 1 is used by connecting the catheter assembly 1 to an external unit 6. The external unit 6 consists of a scanner apparatus 61 which has an external driving source such as a built-in motor, an axial direction moving apparatus 62 which holds the scanner apparatus 61 to move in the horizontal direction (in the axial direction) by a motor, or the like, a control unit 63 which operates to control a motion of the scanner apparatus 61 and the axial direction moving apparatus 62, and a display unit 64 which displays an image of the blood vessel wall obtained by the catheter assembly 1.

Set forth next will be a description of the external unit 6, followed by a description of the configuration of each part of the catheter assembly 1.

The scanner apparatus 61 is connected to the proximal end portion of the catheter assembly 1. Then, the scanner apparatus 61 rotates the driveshaft 3 around the axis of the driveshaft 3 and is axially moved together with the catheter assembly 1 along the axial direction by the axial direction moving apparatus 62. In this manner, it is possible to scan an ultrasonic vibrator (an image obtaining unit) 52 of the driveshaft 3. In addition, it is possible to form an image of the blood vessel wall in the external unit 6, based on information which is obtained from the driveshaft 3 which is sent through the scanner apparatus 61. In this manner, it is possible to obtain a transverse image in the blood vessel, which is an ultrasonic image, at a desired (arbitrary) position with respect to the blood vessel over the whole inner circumference in the circumferential direction of the blood vessel.

The control unit 63, for example, is a personal computer which has a CPU (Central Processing Unit) built-in. The display unit 64, for example, is a liquid crystal display apparatus.

Set forth next is a description of the catheter assembly 1.

As described before, the catheter assembly 1 includes the catheter 2 and the driveshaft 3.

The catheter 2 includes a catheter main body 21 which is flexible or exhibits flexibility and has an elongated shape, and a connector unit 22 which is fixed to the proximal end portion of the catheter main body 21.

A sensor lumen 211 and a guide wire lumen 233 are located in the catheter main and extend along the longitudinal direction of the catheter main body 21. The driveshaft 3 is inserted into and positioned in the sensor lumen 211, and a guide wire 200 is inserted into or positioned in the guide wire lumen 233. In addition, the distal end portion of the catheter main body 21 possesses a reduced diameter unit in which the outer diameter is diametrically reduced toward the distal end.

As described above, the driveshaft 3 is configured to be inserted into and positioned in the sensor lumen 211, and the sensor lumen 211 extends throughout the full length of the catheter main body 21. The portion which is provided with the sensor lumen 211 in the catheter main body 21 is configured as or constitutes a driveshaft insertion unit 210 into which the driveshaft 3 is configured to be inserted.

The driveshaft insertion unit 210 includes or is comprised of a first flexible tube 7 which exhibits flexibility, a second tube 8 at the distal end of the first tube 7 which exhibits flexibility, and a third tube 9 provided at the distal end side of the second tube 8 which also exhibits flexibility. The outer diameter and the inner diameter of the third tube 9 are respectively smaller than the outer diameter and the inner diameter of a first portion 71 (described later) of the first tube 7.

The first tube 7 is an embodiment of a medical tube disclosed here, and is configured to extend from the proximal end of the driveshaft insertion unit 210 to the middle of the distal end side in the driveshaft insertion unit 210. This first tube 7 has a first portion 71, a second portion 72 and a third portion 73 positioned in this order from the proximal end toward the distal end, as described later (refer to FIG. 3). In addition, the third tube 9 is configured as a part of the distal end portion in the driveshaft insertion unit 210 and is fixed to the distal end portion of the first tube 7.

In this example, the inner circumferential surface of the proximal end portion of the third tube 9 is fixed to the outer circumferential surface of the distal end portion of the third portion 73 of the first tube 7. The second tube 8 covers the second portion 72 and the third portion 73 of the first tube 7 and the proximal end portion of the third tube 9. In this example, the inner circumferential surface of the proximal end side of the second tube 8 is fixed to the outer circumferential surface of the second portion 72 of the first tube 7, and the inner circumferential surface of the distal end side of the second tube 8 is fixed to the outer circumferential surface of the third portion 73 of the first tube 7 and the outer circumferential surface of the proximal end portion of the third tube 9. By virtue of the inner circumferential surface of the proximal end portion of the third tube 9 being fixed to the outer circumferential surface of the distal end portion of the third portion 73 of the first tube 7, it is possible to prevent kinks in the catheter main body 21. A method of fixing of each unit described above is not particularly limited, and can include, for example, adhesion by an adhesive agent, fusion such as heat fusion and ultrasonic fusion, and the like are included. In addition, the axial end face at the proximal end of the second tube 8 is butted to the axial end face at the distal end the first portion 71. A more detailed description of the first tube 7 will be set forth below.

As described above, the guide wire 200 is configured to be inserted into and positioned in the guide wire lumen 233, and this guide wire lumen 233 is formed only at the distal end portion of the catheter main body 21 in the present embodiment. The portion provided with the guide wire lumen 233 in the catheter main body 21 is configured as or constitutes a guide wire insertion unit 23 into which the guide wire 200 is inserted.

A liquid Q is introduced into and filled in the sensor lumen 211 in a state in which the driveshaft 3 is inserted (i.e., the driveshaft 3 is positioned in the lumen 211), that is, in an insertion state. By virtue of the liquid Q filling the lumen 211, ultrasonic waves from the ultrasonic vibrator 52 are transmitted to the blood vessel wall and return back to the ultrasonic vibrator 52 from the blood vessel wall again. In this manner, it is possible to obtain an ultrasonic image. The liquid Q is not limited to a particularly liquid. By way of example, the liquid Q can be a physiological salt solution, a contrast medium, and the like.

The sensor lumen 211 has an opening 212 which is open at the distal end of the catheter main body 21. The liquid Q which is filled in the sensor lumen 211 is discharged through the opening 212. In this manner, even if excessive liquid Q is introduced into or filled-in, it is possible to reliably prevent a break of the catheter main body 21 caused thereby.

The opening 212 is open toward a sloping direction with respect to the central axis of the catheter main body 21 in a configuration shown in FIG. 1. But the opening 212 is not limited in this regard. For example, the opening 212 may open toward the central axis direction of the catheter main body 21, that is, the distal end direction.

The catheter main body 21 has the guide wire insertion unit 23, at the distal end portion of the catheter main body 21, into which the guide wire 200 is configured to be inserted. The guide wire insertion unit 23 is comprised of two insertion members 231 and 232 which form a tubular-shape in which both ends of each member are respectively open. The insertion members 231 and 232 are arranged so as to be separated from each other along the longitudinal direction of the catheter main body 21. The guide wire lumen 233 is comprised of the lumen of the guide wire insertion unit 23 and this guide wire lumen 233 is arranged parallel with respect to the sensor lumen 211. The catheter 2 is inserted into the blood vessel in a state in which the guide wire 200 is inserted into the guide wire lumen 233 of the guide wire insertion unit 23, and is a catheter of the so-called "rapid exchange type (short monorail type)" in which it is possible to relatively rapidly perform the extraction and the insertion of the guide wire 200.

The guide wire insertion unit 23 is arranged parallel to the central axis of the catheter main body 21 in a configuration shown in FIG. 1. However, the guide wire insertion unit 23 is not limited in this regard, and for example, may be arranged to be tilted with respect to the central axis of the catheter main body 21.

In addition, in the middle in the longitudinal direction of the insertion member 231 of the distal end side of the guide wire insertion unit 23, a coil (not shown) is embedded. This coil functions as a contrast marker to visually recognize a position of the distal end portion of the catheter 2 under an X-ray illumination. The coil is configured of a metallic material for example, like platinum having radiopaque properties.

The catheter main body 21 is configured by materials having flexibility, the materials thereof are not particularly limited, and for example, thermoplastic resins such as various kinds of thermoplastic elastomers such as styrene-based, polyolefin-based, polyurethane-based, polyester-based, polyamide-based, polyimide-based, polybutadiene-based, transpolyisoprene-based, fluoro rubber-based, chlorinated polyethylene-based thermoplastic elastomers are included, and a resin which is one kind thereof or is a combination of two or more kinds thereof (a polymer alloy, a polymer blend, a laminated body, or the like) can be used.

In addition, in the catheter main body 21, the vessel wall of the catheter main body 21 may be a single layer or may be a laminated body in which a plurality of layers are laminated.

The connector unit 22 which is fixed to the proximal end portion of the catheter main body 21 is configured as a hard tubular body. This connector unit 22 is connected to the scanner apparatus 61 of the external unit 6.

A method of fixing the connector unit 22 with respect to the catheter main body 21 is not particularly limited. Examples include a method involving adhesion (adhesion by an adhesive agent and a solvent), a method by fusion (heat fusion, high frequency fusion, ultrasonic fusion, or the like), and the like.

In the middle in the longitudinal direction of the connector unit 22, a projecting liquid injection port 221 is formed. It is possible, for example, to inject the liquid Q from the liquid injection port 221 using a syringe. Then the injected liquid Q is filled in the sensor lumen 211 of the catheter main body 21.

A rotary support unit 222 which rotatably supports the driveshaft 3 is provided at the proximal end portion of the connector unit 22.

In addition, at the proximal end portion of the connector unit 22, a seal member 25 is arranged at the distal end side of the rotary support unit 222. The seal member 25 is configured as an elastic body which is ring-shaped. In this manner, the seal member 25 can prevent a gap from being generated between the inner circumferential portion of the connector unit 22 and the outer circumferential portion of the driveshaft 3. The seal member 25 thus maintains liquid-tightness, therefore, it is possible to prevent the liquid Q from leaking toward the proximal end direction.

The constituent materials of the connector unit 22 are not particularly limited, and for example, various kinds of resins such as polyvinyl chloride, polyethylene, polypropylene, cyclic polyolefin, polystyrene, poly-(4-methylpentene-1), polycarbonate, an acrylic resin, an acrylonitrile-butadiene-styrene copolymer, polyester such as polyethylene terephthalate and polyethylene naphthalate, a butadiene-styrene copolymer and polyamide (for example, nylon 6, nylon 6•6, nylon 6•10, and nylon 12) are included.

The connector unit 22 is a connector unit in which three tubular bodies are connected along the longitudinal direction in a configuration shown in FIG. 1. However, the, connector unit 22 is not limited in this regard, and for example, may be a connector unit which is configured by one tubular body.

The driveshaft 3 is inserted into and positioned in the sensor lumen 211 of the catheter main body 21 of the catheter 2. The driveshaft 3 in this insertion state is rotated around its central axis by a motion or operation of the scanner apparatus 61.

The driveshaft 3 includes an elongated shaft 4 which is a body of the driveshaft 3, a housing 51 which is fixed to the distal end portion of the shaft 4, the ultrasonic vibrator 52 which is stored in the housing 51, a connector unit 53 fixed to the proximal end portion of the shaft 4. The driveshaft 3, the housing 51, the ultrasonic vibrator 52, and the connector unit 53 constitute an imaging means 5 for imaging an image of the blood vessel wall.

The shaft 4 has torque transmissibility so that the shaft 4 can reliably transmit a turning force by a motion of the scanner apparatus 61 to the ultrasonic vibrator 52. This shaft 4, for example, is formed by closely winding a metal wire such as stainless steel in a coil-shape (refer to FIG. 2). This metal wire may be multiply-wound.

The outer diameter of this shaft 4 is smaller than the diameter of the sensor lumen 211. In this manner, a gap 213 is formed between the outer circumferential surface of the shaft 4 and the inner circumferential surface of the catheter main body 21. The liquid Q which is injected from a liquid injection port 221 of the catheter 2 flows down through the gap 213 and is discharged from the opening 212.

The housing 51 is fixed to the distal end portion of the shaft 4, for example, by an adhesive agent. The housing 51 is configured as a cylindrical body made from metal such as a stainless steel and a through hole 511 penetrates through the wall part of the cylindrical body. From the through hole 511, the ultrasonic vibrator 52 is exposed. The diameter of the housing 51 is substantially the same as the outer diameter of the shaft 4 or slightly larger than that.

The ultrasonic vibrator 52 is fixed in the housing 51 so that the center of gravity of the ultrasonic vibrator 52 is positioned on the central axis of the shaft 4. In this manner, the ultrasonic vibrator 52 can be rotated together with the shaft 4. The ultrasonic vibrator 52 possesses a rectangular or circular-shape, in a plane view, and is an ultrasonic vibrator in which an electrode is formed on both surfaces of a piezoelectric body which is configured by PZT (lead zirconate titanate) by deposition, printing, or the like. In this manner, in the state facing the blood vessel wall, it is possible to emit ultrasonic waves from the ultrasonic vibrator 52 as well as to receive the reflected waves of the ultrasonic waves on the blood vessel wall. That is, it is possible to perform the transmission and reception of the ultrasonic waves. By this transmission and reception, it is possible to fetch or obtain an image of the blood vessel wall. This image is an image in which the ultrasonic waves is transmitted from the ultrasonic vibrator 52 and the distance to the blood vessel wall is measured in time until the reflected waves return back to the ultrasonic vibrator 52 again to visualize the state of the blood vessel wall.

A plurality of signal lines connected to and extending from the ultrasonic vibrator 52 are located in the shaft 4 and are electrically connected to the connector unit 53.

The connector unit 53 is connected to the scanner apparatus 61, and it is possible to directly receive a turning force from the scanner apparatus 61. This connector unit 53 is configured by a cylinder made of metal having conductivity such as copper. In this manner, it is also possible to electrically connect the connector unit 53 to the scanner apparatus 61, and it is possible to send an image signal from the ultrasonic vibrator 52 to the display unit 64 through the scanner apparatus 61. Then, an image of the blood vessel wall is displayed at the display unit 64.

Set forth next is a description of the first tube 7.

Figure 3:
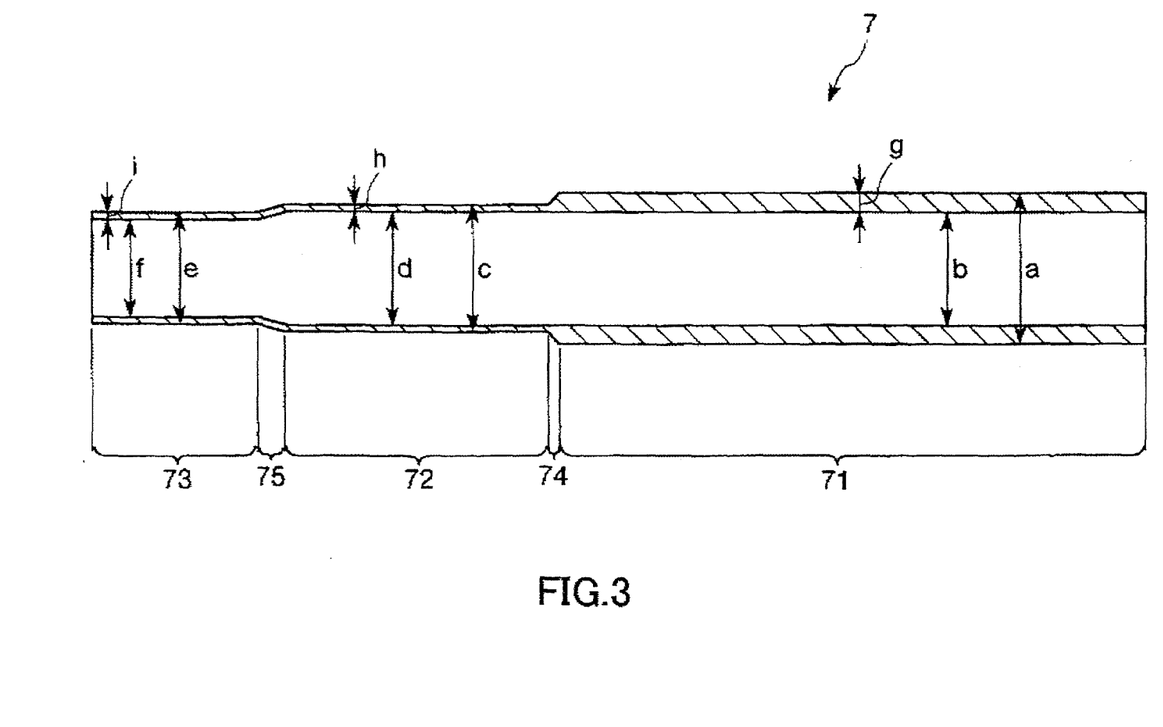
FIG. 3 is a longitudinal cross-sectional view showing a first tube in a catheter assembly shown in FIG. 1, that is, the first embodiment of a medical tube disclosed here.

The first tube 7 is a medical tube in which the first portion 71, the second portion 72 and the third portion 73 are arranged in this order from the proximal end of the first tube 7 toward the distal end of the first tube 7 and which is made of a resin, as shown in FIG. 3

The outer diameter c of the first tube 7 at the second portion 72 is smaller than the outer diameter a of the first portion 71, and the inner diameter d at the second portion 72 of the first tube 7 is substantially equal to the inner diameter b of the first portion 71. Therefore, the thickness h of the second portion 72 and the thickness i of the third portion 73 are substantially equal.

The outer diameter e at the third portion 73 of the first tube 7 and the inner diameter f at the third portion 73 of the first tube 7 are respectively smaller than the outer diameter c and the inner diameter d at the second portion 72 of the first tube 7.

In addition, the outer diameter a and the inner diameter b of the first portion 71, the outer diameter c and the inner diameter d of the second portion 72, and the outer diameter e and the inner diameter f of the third portion 73 are respectively constant along the longitudinal direction of the first tube 7.

In addition, in a configuration shown in FIG. 3, the thickness h of the second portion 72 and the thickness i of the third portion 73 are set to be substantially equal. It is also possible though for the thickness h of the second portion 72 and the thickness i of the third portion 73 to be different.

In addition, the first tube 7 has a first taper unit 74 in which the outer diameter is gradually decreased from the proximal end toward the distal end between the first portion 71 and the second portion 72.

The first tube 7 also has a second taper unit 75 in which the outer diameter and the inner diameter are gradually decreased from the proximal end toward the distal end between the second portion 72 and the third portion 73.

According to this configuration of the first tube 7, it is possible to make the outer diameter e of the third portion 73 relatively small while making the outer diameter a of the first portion 71 relatively large and making the inner diameter f of the third portion 73 which has the smallest inner diameter sufficiently large. In this manner, the inner circumferential surface of the proximal end portion of the third tube 9 in which the inner diameter is relatively small can be reliably fixed to the outer circumferential surface of the distal end portion of the third portion 73 of the first tube 7.

The outer circumferences of the second portion 72 and the third portion 73 are the portions on which other tubes, that is, the second tube 8 and the third tube 9, are coated or axially overlap. The outer diameter of the second tube 8, which is provided on the outer circumference of the second portion 72, and the outer diameter a of the first portion 71 are substantially equal (refer to FIG. 2).

Here, the size of each unit of the first tube 7 is not, respectively, particularly limited, and is appropriately set according to the conditions. By way of example, the sizes described below are preferable.

The outer diameter a of the first portion 71 of the first tube 7 is preferably from approximately 1.02 mm to 1.10 mm, and more preferably from approximately 1.04 mm to 1.08 mm.

In addition, the inner diameter b of the first portion 71 is preferably from approximately 0.70 mm to 0.78 mm, and more preferably from approximately 0.72 mm to 0.76 mm.

In addition, the outer diameter c of the second portion 72 is preferably from approximately 0.82 mm to 0.90 mm, and more preferably from approximately 0.84 mm to 0.88 mm.

In addition, the inner diameter d of the second portion 72 is preferably from approximately 0.70 mm to 0.78 mm, and more preferably from approximately 0.72 mm to 0.76 mm.

In addition, the outer diameter e of the third portion 73 is preferably from approximately 0.71 mm to 0.79 mm, and more preferably from approximately 0.73 mm to 0.77 mm.

In addition, the inner diameter f of the third portion 73 is preferably from approximately 0.62 mm to 0.68 mm, and more preferably from approximately 0.64 mm to 0.66 mm.

In addition, the thickness g of the first portion 71 is preferably from approximately 0.12 mm to 0.19 mm, and more preferably from approximately 0.14 mm to 0.17 mm.

In addition, the thickness h of the second portion 72 is preferably from approximately 0.02 mm to 0.10 mm, and more preferably from approximately 0.04 mm to 0.08 mm.

In addition, the thickness i of the third portion 73 is preferably from approximately 0.01 m to 0.09 m, and more preferably from approximately 0.03 mm to 0.07 mm.

In addition, the thickness h of the second portion 72 is preferably from approximately 11% to 83%, and more preferably from approximately 24% to 57%, of the thickness g of the first portion 71.

In addition, the outer diameter c of the second portion 72 is preferably from approximately 76% to 88%, and more preferably from approximately 79% to 85%, of the outer diameter a of the first portion 71.

In addition, the outer diameter e of the third portion 73 is preferably from approximately 79% to 96%, and more preferably from approximately 83% to 92%, of the outer diameter c of the second portion 72.

In addition, the inner diameter f of the third portion 73 is preferably from approximately 78% to 99%, and more preferably from approximately 83% to 93%, of the inner diameter d of the second portion 72.

In addition, in the embodiment illustrated by way of example in a configuration shown in FIG. 3, the outer diameter e of the third portion 73 and the inner diameter d of the second portion 72 are substantially equal. That is, the third portion 73 is shifted radially inwardly by a distance equalling the thickness i of the third portion 73. It is to be understood that the outer diameter e of the third portion 73 and the inner diameter d of the second portion 72 may be different.

The first tube 7 is a tube in which the first portion 71, the second portion 72, and the third portion 73 are integrally formed of the same material.

In addition, the constituent materials of the first tube 7 are not particularly limited as long as the constituent materials are resin materials having flexibility, and for example, thermoplastic resins such as polyolefin such as polyethylene and polypropylene, polyvinyl chloride, polyvinylidene chloride, polyurethane, polyvinylidene fluoride, polyolefin halide, polyethylene terephthalate, polybutylene terephthalate, polycarbonate, polyether ether ketone, a silicone rubber, and various kinds of thermoplastic elastomers such as styrene-based, polyolefin-based, polyurethane-based, polyester-based, polyamide-based, polyimide-based, polybutadiene-based, transpolyisoprene-based, fluoro rubber-based, and chlorinated polyethylene-based thermoplastic elastomers are included, and among these, a resin which is one kind thereof or a combination of two or more kinds thereof (a polymer alloy, a polymer blend, a laminated body, or the like) can be used. Note that, among these, polyether ether ketone is preferable. The reason is that polyether ether ketone is relatively hard and it is difficult for the coagulated blood to adhere when the blood coagulates.

Set forth next is a description of a method of manufacturing the first tube 7.

Figure 4:
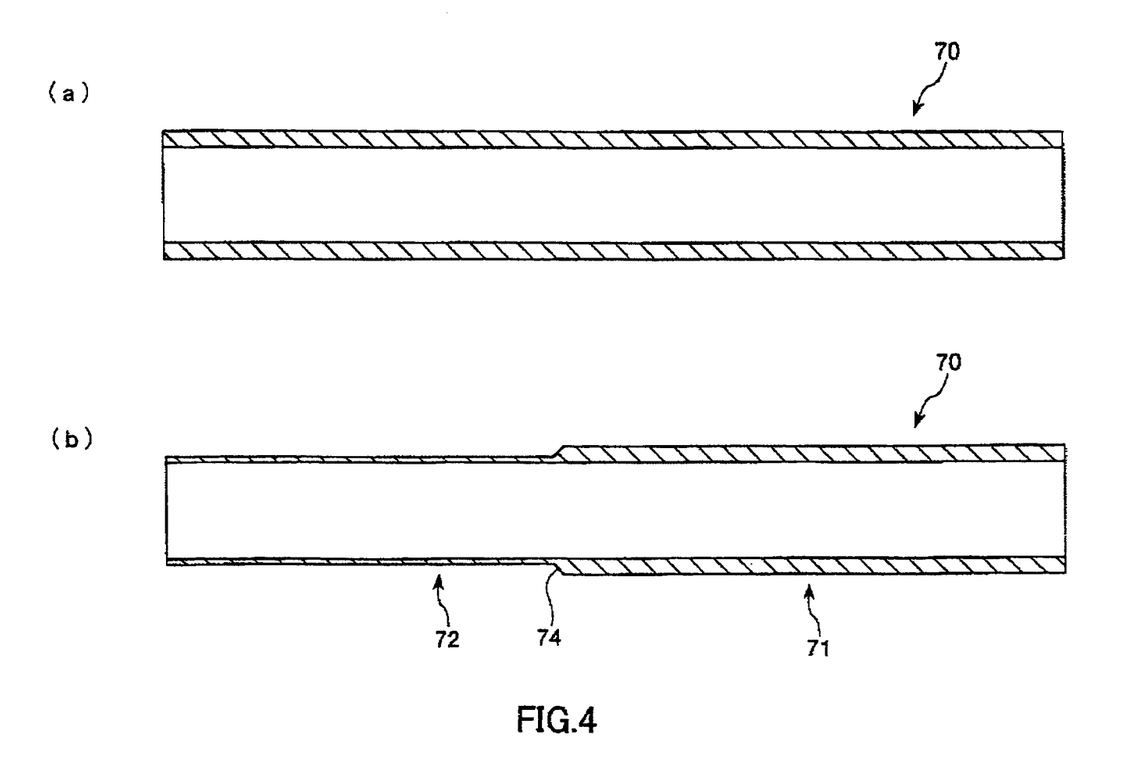
FIG. 4 is a longitudinal cross-sectional view for explaining a manufacturing process of the first tube shown in FIG. 1.

First, a tube for processing 70 which is a tube before processing is prepared, as shown in FIG. 4 (a). This tube for processing 70 has a definite outer diameter and a definite inner diameter. In addition, the outer diameter of the tube for processing 70 is substantially equal to the outer diameter a of the first portion 71 of the first tube 7, the inner diameter is substantially equal to the inner diameter b of the first portion 71, and the thickness is substantially equal to the thickness g of the first portion 71.

First Process

The outer circumferential surface of the distal end portion of the tube for processing 70 is physically or chemically ground, as shown in FIG. 4 (a). To carry out the physical grinding, for example, a grinding apparatus, or the like is used. In addition, examples of the chemical grinding include etching and the like. In the first process, the portion in which the tube for processing 70 is not ground becomes the first portion 71 and the portion which is ground becomes the second portion 72. In addition, the first taper unit 74 is formed between the first portion 71 and the second portion 72.

Second Process

Thermoforming is conducted, with respect to the portion of the distal end side from the middle of the ground portion of the tube for processing 70, and the outer diameter and the inner diameter of the portion of the distal end side from the middle of the ground portion are more reduced than those of the portion of the proximal end side from the middle of the ground portion, as shown in FIG. 3. The third portion 73 and the second taper unit 75 are formed by thermoforming to obtain the first tube 7.

In addition, in thermoforming described above, a forming die having the inner diameter which is substantially equal to the outer diameter e of the third portion 73 and a core bar having the outer diameter which is substantially equal to the inner diameter f of the third portion 73 are used and heating is performed at the predetermined temperature. The heating temperature is not particularly limited, and is appropriately determined according to the conditions. As an example, approximately 230° C. to 270° C. is preferable, and approximately 240° C. to 260° C. is more preferable.

Figure 5:
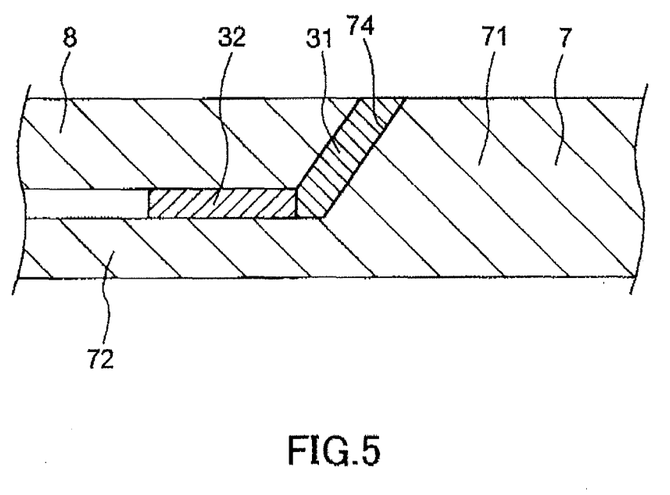
FIG. 5 is an enlarged longitudinal cross-sectional view of an area [B] surrounded with a broken line in FIG. 2.

In addition, the proximal end portion of the second tube 8 is adhered to the second portion 72 of the first tube 7 and the first taper unit 74 by an adhesive agent, as shown in FIG. 5.

Specifically, a first adhesive agent 31 is provided at a joined part between the second tube 8 and the first tube 7, that is, between the proximal end surface of the second tube 8 and the first taper unit 74, and a second adhesive agent 32 is provided between the second tube 8 and the second portion 72 in the vicinity of the joined part described above.

The first adhesive agent 31 and the second adhesive agent 32 are not particularly limited, however, it is preferred that a reaction system adhesive agent be used. An example of a reaction system adhesive agent includes a radiation curable adhesive agent which is cured by irradiating with radiation such as ultraviolet rays, and the like.

When the proximal end portion of the second tube 8 is adhered to the second portion 72 and the first taper unit 74, first, the second adhesive agent 32 to be cured is injected from a gap between the proximal end surface of the second tube 8 and the first taper unit 74.

This second adhesive agent 32 is preferably an adhesive agent in which the viscosity is relatively low. In this manner, it is possible to inject the second adhesive agent 32 into more distal end side and enhance the joint strength between the second tube 8 and the second portion 72.

As the second adhesive agent 32, for example, it is preferred that an acrylic resin-based adhesive agent, or the like be used.

Next, the first adhesive agent 31 is injected into a gap between the proximal end surface of the second tube 8 and the first taper unit 74 and is cured to seal the gap.

This first adhesive agent 31 is preferably an adhesive agent in which the viscosity is relatively high and which is chemical-resistant. In this manner, when the first adhesive agent 31 is injected into the gap described above, it is difficult for the first adhesive agent 31 to flow from the gap to other portion, therefore, it is possible to certainly seal the gap. In addition, since the surface of the catheter main body 21 is treated by the predetermined chemicals, when the treatment is conducted, it is possible to certainly prevent the chemicals from entering into the gap described above.

As the first adhesive agent 31, for example, it is preferred that an epoxy resin-based adhesive agent, an urethane resin-based adhesive agent, or the like is used.

As explained above, according to the first tube 7, it is possible to make the outer diameter e of the third portion 73 relatively small while making the outer diameter a of the first portion 71 relatively large and making the inner diameter f of the third portion 73 which has the smallest inner diameter sufficiently large. In this manner, the inner circumferential surface of the proximal end portion of the third tube 9 in which the outer diameter is relatively small can be reliably fixed to the outer circumferential surface of the distal end portion of the third portion 73 of the first tube 7.

In addition, according the method of manufacturing the first tube 7, it is possible to rather easily and reliably manufacture the first tube 7.

Descriptions of the medical tube, the catheter and the method of manufacturing the medical tube disclosed here have been given based on an embodiment shown in the drawing figures. However, the present invention is not limited in this regard, and the configuration of each unit can be substituted by another appropriate configuration having a similar function. In addition, other structural components and processes may be added.

The catheter main body is not limited to a catheter having a distal end opening which is open at the distal end as an outlet of a liquid, and may be, for example, a catheter main body having a side hole which penetrates into the side wall of the distal end portion.

In addition, an image which is obtained by the catheter assembly is not limited to an ultrasonic image, and may be, for example, an image which is optically obtained, that is, an image which is obtained by emitting and receiving the light. For example, the catheter may be a catheter which is used for an image by the light signal, in particular, an optical coherent tomography apparatus (OCT), and an optical frequency domain imaging apparatus (OFDI) which is an improved version of the OCT apparatus. In this case, after an interference light is generated by irradiating a biological tissue with near infrared rays which are emitted from the distal end portion of the driveshaft and interfering a reflected light from the biological tissue with a reference light, it is possible to generate a cross-sectional image in the body lumen such as the blood vessel based on the interference light.

Disclosed here is a medical tube in which the outer diameter of the proximal end side is relatively large, and the outer diameter of the distal end side is relatively small while securing the inner diameter having sufficient size at the distal end side. In addition, according to the disclosure here, such a medical tube can be rather easily and reliably manufactured.

The detailed description above describes a medical tube, a catheter and a method of manufacturing a medical tube disclosed by way of example. The invention is not limited, however, to the precise embodiments and variations described. Various changes, modifications and equivalents can effected or implemented by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter comprising:
a first tube possessing a proximal end and a distal end, the first tube possessing a longitudinally extending first portion, a longitudinally extending second portion and a longitudinally extending third portion arranged in this order in a direction from a proximal end side toward a distal end side of the first tube;
the first, second and third portions each possessing an outer surface;
the first portion possessing a proximal end part that is a part of the first portion axially closest to the second portion;
the entire longitudinal extent of the first portion, the entire longitudinal extent of the second portion and the entire longitudinal extent of the third portion of the tube being made of a single common resin;
the first portion, the second portion and the third portion each possessing an inner diameter and an outer diameter;
the outer diameter of the second portion being smaller than the outer diameter of the first portion, and the inner diameter of the second portion being substantially equal to the inner diameter of the first portion;
the inner diameter of the third portion being smaller than the inner diameter of the second portion, and the outer diameter of the third portion being constant and being smaller than the outer diameter of the second portion;
a second tube in contact with and covering both the entire longitudinal extent of the outer surface of the second portion and the entire longitudinal extent of the outer surface of the third portion;
the second tube not covering the outer surface of the proximal end part of the first portion;
the second tube possessing a distal end portion that extends distally beyond a distal-most end of the third portion of the first tube;
a third tube that possesses a proximal end portion, the proximal end portion of the third tube being covered by a distal end portion of the second tube and covering a distal end portion of the third portion of the first tube; and
the third tube extending distally beyond a distal-most end of the second tube and extending distally beyond a distal-most end of the first tube.

2. The catheter according to claim 1, wherein the tube comprises a taper portion between the first portion and the second portion, the taper portion possessing a proximal end and a distal end, the taper portion possessing an outer diameter that gradually decreases in a direction from the proximal end side toward the distal end side between the first portion and the second portion.

3. The catheter according to claim 1, wherein the tube comprises a taper portion between the second portion and the third portion, the taper portion possessing a proximal end and a distal end, the taper portion possessing an outer diameter and an inner diameter that gradually decrease in a direction from the proximal end side toward the distal end side between the second portion and the third portion.

4. The catheter according to claim 1, wherein the outer surface of the proximal end part of the first portion is exposed.

5. The catheter according to claim 1, wherein a wall thickness of the second portion is 11% to 83% of a wall thickness of the first portion.

6. The catheter according to claim 1, wherein an outer diameter of the second tube at the second portion is substantially equal to the outer diameter of the first portion.

7. The catheter according to claim 1, wherein the tube possesses a distal-most end and a proximal-most end, and the second tube possesses a distal-most end that extends distally beyond the distal-most end of the tube.

8. A catheter assembly comprising:
a catheter in combination with a driveshaft that is positionable in the catheter;
the driveshaft comprising: an elongated shaft; a housing fixed to a distal end portion of the shaft; and an ultrasonic vibrator stored in the housing;
the catheter comprising:
an elongated first tube having a longitudinal extent and possessing a proximal end and a distal end, the first tube possessing a first portion, a second portion and a third portion arranged in this order in a longitudinal direction from a proximal end side toward a distal end side of the tube, the tube being made of resin;
the first portion, the second portion and the third portion each possessing an inner diameter and an outer diameter;
the outer diameter of the first portion being greater than the outer diameter of the second portion, and the inner diameter of the second portion being substantially equal to the inner diameter of the first portion;
the inner diameter of the third portion being smaller than the inner diameter of the second portion, and the outer diameter of the third portion being smaller than the outer diameter of the second portion;
the outer diameter of the third portion and the inner diameter of the second portion being substantially equal; and
the entire longitudinal extent of the first portion, the entire longitudinal extent of the second portion and the entire longitudinal extent of the third portion being formed only of a single resin;
a second tube in contact with and covering both the entire longitudinal extent of the outer surface of the second portion of the first tube and the entire longitudinal extent of the outer surface of the third portion of the first tube;
the second tube not covering the outer surface of the proximal end part of the first portion;
the second tube possessing a distal end portion that extends distally beyond a distal-most end of the third portion of the first tube;
a third tube that possesses a proximal end portion positioned between a portion of the second tube of the first tube and a portion of the third portion of the first tube so that an outer surface of the proximal end portion of the third tube faces an inner surface of the portion of the second tube and an inner surface of the proximal end portion of the third tube faces the outer surface of portion of the third portion of the first tube;
the third tube extending distally beyond a distal-most end of the second tube and extending distally beyond a distal-most end of the first tube; and
the second tube extending distally beyond a distal-most end of the first tube.

9. The catheter according to claim 4, wherein the outer diameter of the second portion of the first tube is 76% to 88% of the outer diameter of the first portion of the first tube.

10. The catheter according to claim 4, wherein a portion of the second tube overlies and is in contact with the outer surface of the third portion of the first tube, and a portion of the second tube overlies and is spaced from the outer surface of the third portion of the first tube.

11. The catheter according to claim 4, further comprising a first taper portion between the first and second portions of the first tube, the second tube possessing a proximal-most end located at the first taper portion, further comprising a third tube made entirely of a single resin material, portions of the first tube, the second tube and the third tube axially overlapping one another, a proximal-most end of the third tube being distal of a distal-most end of the second portion of the first tube.

12. The catheter according to claim 1, wherein the outer diameter of the second portion of the first tube is 76% to 88% of the outer diameter of the first portion of the first tube.

13. The catheter according to claim 1, wherein the proximal end portion of the third tube that covers the distal end portion of the third portion of the first tube possesses an inner diameter greater than an inner diameter of a portion of the third tube located distally beyond the distal-most end of the second tube.

14. The catheter according to claim 1, wherein a portion of the second tube overlies and is in contact with the outer surface of the third portion of the first tube, and a portion of the second tube overlies and is spaced from the outer surface of the third portion of the first tube.

15. The catheter according to claim 8, wherein the outer diameter of the second portion of the first tube is 76% to 88% of the outer diameter of the first portion of the first tube.

16. The catheter according to claim 8, wherein the proximal end portion of the third tube that covers the distal end portion of the third portion of the first tube possesses an inner diameter greater than an inner diameter of a portion of the third tube located distally beyond the distal-most end of the second tube.

17. The catheter according to claim 8, wherein a portion of the second tube overlies, faces towards and is in contact with the outer surface of the third portion of the first tube, and a portion of the second tube overlies, faces towards and is spaced from the outer surface of the third portion of the first tube.

* * * * *